United States Patent
Williams et al.

(10) Patent No.: US 6,755,979 B2
(45) Date of Patent: Jun. 29, 2004

(54) PEROXIDE IMPURITIES REMOVAL

(75) Inventors: Carl L. Williams, Houston, TX (US); Shaw-Chan Lin, West Chester, PA (US); David W. Leyshon, West Chester, PA (US); Lawrence M. Candela, Havertown, PA (US)

(73) Assignee: ARCO Chemical Technology, L.P., Greenville, DE (US)

( * ) Notice: Subject to any disclaimer, the term of this patent is extended or adjusted under 35 U.S.C. 154(b) by 32 days.

(21) Appl. No.: 10/219,417

(22) Filed: Aug. 15, 2002

(65) Prior Publication Data

US 2004/0031763 A1 Feb. 19, 2004

(51) Int. Cl.⁷ .................................................. C02F 1/58
(52) U.S. Cl. ...................... 210/750; 210/758; 210/763; 95/204
(58) Field of Search ................................ 210/750, 758, 210/759, 763; 95/204; 568/569

(56) References Cited

U.S. PATENT DOCUMENTS

| | | |
|---|---|---|
| 3,351,635 A | 11/1967 | Kollar |
| 4,066,706 A | 1/1978 | Schmidt |
| 5,993,673 A | 11/1999 | Evans et al. |

*Primary Examiner*—Frank M. Lawrence
(74) *Attorney, Agent, or Firm*—William C. Long

(57) ABSTRACT

A propylene oxide/styrene monomer aqueous purge stream is contacted with a catalyst at conditions effective to decompose peroxides contained therein, and oxygen formed by the decomposition swept from the decomposition with a nitrogen vapor stream from ethylbenzene oxidation.

4 Claims, 1 Drawing Sheet

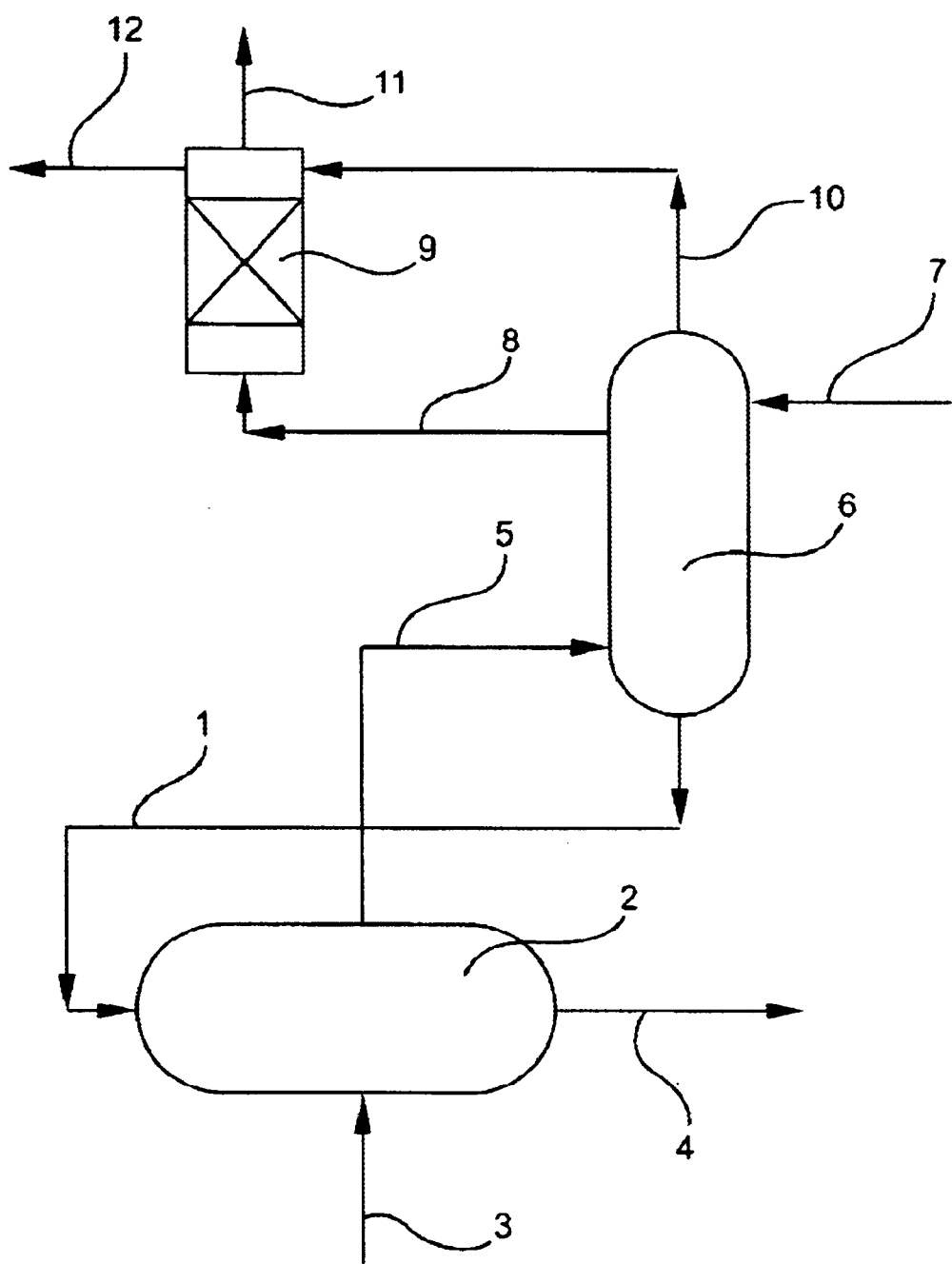

PEROXIDE IMPURITIES REMOVAL

BACKGROUND OF THE INVENTION

1. Field of the Invention

The present invention relates to a process for removing peroxides from peroxide containing aqueous waste streams such as those from the propylene oxide/styrene monomer technology so that the treated stream can be further processed prior to its disposal.

2. Description of the Prior Art

The Oxirane process for the production of propylene oxide and styrene monomer is a process of very great commercial importance. The basic patent describing this process is U.S. Pat. No. 3,351,635. In a version of the process, ethylbenzene is oxidized to ethylbenzene hydroperoxide, the ethylbenzene hydroperoxide is catalytically reacted with propylene to form propylene oxide and 1-phenyl ethanol, and the 1-phenyl ethanol is dehydrated to form styrene monomer.

In practice of the process there are a number of separation and recovery steps and various purge streams are formed which must be disposed of in the face of ever increasing environmental concerns. In various instances, disposal practices which were permitted in the past may, in the future, no longer be permitted. Accordingly, considerable efforts are being directed to bring about improvements in procedures used to treat propylene oxide/styrene monomer purge streams.

One such purge stream is an acidic wastewater removed as a distillation sidestream. In the Oxirane propylene oxide and styrene monomer process, ethylbenzene is reacted with molecular oxygen to produce ethylbenzene hydroperoxide. See, for example, U.S. Pat. No. 4,066,706. Vapor from the oxidation is contacted with cool ethylbenzene in order to absorb contained ethylbenzene from the vapors and to effect economies of heat recovery. Normally a liquid acidic aqueous sidestream is recovered from the contact/absorption zone of the absorber and an overhead vapor stream mainly comprised of nitrogen is also recovered. The acidic wastewater contains in addition to water and various organic acids, significant amounts of peroxidic materials. Consideration has been given to biotreatment of such streams but the contained organics tend to flash in a biopond exceeding VOC limits. First stripping organics before biotreatment is an option but this would result in dangerous concentrations of peroxides forming within the stripper.

In U.S. Pat. No. 5,993,673, a procedure for decomposing peroxidic materials is shown wherein the acidic aqueous stream is contacted with a solid iron promoted alumina catalyst to effect such decomposition. It is disclosed that a nitrogen sweep gas is employed to remove oxygen which is formed by the peroxide decomposition.

In such systems, the provision of a independent source of nitrogen represents a significant process expense. In accordance with the present invention, however, nitrogen vapor from the oxidizer is used to sweep the oxygen which results from peroxide decomposition thus avoiding the need and expense of separately purchased nitrogen.

SUMMARY OF THE INVENTION

In accordance with the invention, acidic aqueous process streams containing organic acids, peroxidic materials and ethylbenzene are contacted with a catalyst at conditions effective to decompose the peroxidic materials and the oxygen formed by the decomposition is swept using at least a portion of the nitrogen vapor effluent from the ethylbenzene oxidation whereby the formation of explosive gas mixtures is avoided.

BRIEF DESCRIPTION OF THE DRAWING

The attached drawing illustrates schematically practice of the invention.

DETAILED DESCRIPTION

The process of the invention is especially applicable to treatment of aqueous acidic purge streams from propylene oxide/styrene monomer production. Such streams are predominantly comprised of water, organic acids, peroxidic components, and ethylbenzene. Generally the purge streams comprise by weight at least 70% water, up to 20% peroxidic components, up to about 30% organic acids, and up to about 1% ethylbenzene. Generally the pH is about 1.5–3.

The invention can perhaps best be described by reference to the accompanying schematic drawing. Ethylbenzene is fed via line 1 to oxidation zone 2 wherein the ethylbenzene is oxidized in the liquid phase to form ethylbenzene hydroperoxide. Reactant gases comprised of molecular oxygen and inert nitrogen as in air are introduced to zone 2 via line 3. Illustrative conditions for carrying out the oxidation are described, for example, in U.S. Pat. No. 4,066,706 the disclosure of which is incorporated herein by reference.

A liquid reaction product stream comprised of ethylbenzene hydroperoxide is removed from zone 2 via line 4 and this stream can be used in the Oxirane process to react with propylene to form propylene oxide (not shown).

During the ethylbenzene oxidation, a vapor stream comprised of nitrogen and ethylbenzene together with water, acids and various peroxidic materials is separated via line 5 from zone 2 and passes to economizer 6 which is a conventional vapor/liquid contact zone. Relatively cool liquid ethylbenzene is fed to zone 6 by means of line 7 and in zone 6 the liquid ethylbenzene is heated by intimate contact with vapors from zone 2 while absorbing contained ethylbenzene. The heated liquid ethylbenzene stream passes from zone 6 via line 1 to oxidation zone 2.

An aqueous acidic liquid sidestream is removed from zone 6 via line 8 and is passed to peroxide decomposition zone 9 wherein catalytic decomposition of contained peroxidic materials takes place. The decomposition procedure used can employ a solid catalyst as described in U.S. Pat. No. 5,993,673 the disclosure of which is incorporated herein by reference.

In addition to solid decomposition catalysts such as the iron promoted alumina catalyst of U.S. Pat. No. 5,993,673, various heterogeneous and homogeneous catalysts can be employed in the decomposition. An especially preferred procedure is to use Fe (III) acetylacetonate as catalyst in which case the catalyst is appropriately added as a solution of the catalyst in methyl benzyl alcohol, acetophenone or ethylbenzene, or a mixture of two or more of these.

Where homogeneous liquid phase decomposition procedures are employed, catalyst concentrations illustratively of 2 to 10 ppm by weight as Fe are employed. Decomposition temperatures of 30 to 100° C. are useful and residence times in the decomposition zone of 5 to 60 min. are preferred.

Although Fe (III) acetylacetonate is especially useful other soluble catalysts, preferably comprised of transition metals, can be used. Examples are $CuSO_4$, $Ni(OAc)_2$, $(NH_4)_2MoO_4$, $Fe(NO_3)_3$ and the like.

An essential feature of the process of this invention is the use of at least a portion of the nitrogen vapor stream from zone 6 as a sweep gas to dilute and remove oxygen generated by peroxidic material decomposition from decomposition zone 9 and to avoid the formation of gas mixtures which are flammable or explosive.

The vapor stream mainly comprised of nitrogen passes from zone 6 as an overhead stream via line 10 to the upper part of zone 9 and the vapor stream comprised of the nitrogen plus oxygen formed by peroxide decomposition is separated via line 11. An aqueous purge stream depleted in peroxidic components is separated via line 12 and can be further treated by conventional procedures.

As a result of the above process, substantial savings are achieved as compared to procedures where a purchased inert gas is used for the oxygen sweep.

The invention is further illustrated by the following examples.

EXAMPLE 1

Referring to the Figure, ethylbenzene is fed at the rate of 1,370,000 lbs/hr via line 1 to oxidation zone 2 wherein at 160° C. and 30 psig the ethylbenzene is reacted with molecular oxygen to form ethylbenzene hydroperoxide. Oxidizing gas comprised of 21 mol % oxygen and 79 mol % nitrogen is fed to zone 2 via line 3 at the rate of 120,000 lb/hr.

Liquid oxidate is removed from zone 2 via line 4 at the rate of 1,070,000 lbs per hour. The oxidate contains 8 wt % ethylbenzene hydroperoxide and this oxidate is reacted with propylene to form propylene oxide (not shown).

A vapor stream comprised by weight of 66% ethylbenzene, 32% nitrogen, 0.4% water, 1% oxygen and 0.6% other materials is passed at the rate of 5,050,000 lbs/hr from zone 2 via line 5 to vapor/liquid contact zone 6. Ethylbenzene is fed at the rate of 1,180,000 lbs/hr to zone 6 via line 7 at 40° C., and in zone 6 is intimately contacted with the vapors from zone 2 a the rate of 5,050,000 lbs/hr.

A liquid ethylbenzene stream at 130° C. is passed from zone 6 via line 1 to oxidation zone 2.

A liquid acidic aqueous purge stream is removed from zone 6 via line 8 and passes at the rate of 2500 lbs/hr to decomposition zone 9. The composition by weight of this liquid stream is 83% water, 6% organic acids, 9% peroxidic materials, 0.1% ethylbenzene and 1.9% others.

Decomposition zone 9 is packed with an iron promoted alumina catalyst such as described in U.S. Pat. No. 5,993,673 and the acidic aqueous purge stream is contacted at 80° C. and 5 psig with the catalyst, which conditions are effective to decompose the peroxidic materials in the aqueous purge.

Vapors are removed overhead from zone 6 and about 98000 lbs/hr are passed via line 10 to zone 9. These vapors comprise by weight about 93% nitrogen, 3% oxygen, 3% ethylbenzene and 1% others and are effective to sweep the oxygen formed by peroxide decomposition from the aqueous liquid purge. A vapor stream by weight of 93% nitrogen, 3% ethylbenzene, 3.1% oxygen and 0.9% others is removed from zone 9 via line 11 at the rate of 98000 lbs/hr and this stream can be flared. The acidic aqueous liquid purge stream substantially free of peroxidic materials is removed at the rate of 2500 lbs/hr via line 12 and this stream can be further treated by conventional procedures.

EXAMPLE 2

Example 1 is repeated except that decomposition zone 9 is comprised of a baffled reaction zone adapted for liquid plug flow and for a vapor sweep in the upper part. The liquid stream introduced via line 8 is admixed with 0.07 lb/hr of iron (III) acetyl acetonate (CAS 14024-18-1) and passes in plug flow through decomposition zone 9 at 60°0 C. and 27 psig, residence time being 20 min. The vapor stream introduced via line 10 passes through the upper section of zone 9 sweeping with it the oxygen formed by peroxide decomposition.

We claim:

1. A process for purifying an acidic aqueous purge stream from propylene oxide/styrene monomer production containing organic acids, peroxidic materials and ethylbenzene which production included the steps of oxidizing ethylbenzene to ethylbenzene hydroperoxide and recovering separately a vapor stream comprising nitrogen and a liquid aqueous purge stream, and catalytically decomposing peroxidic materials in said purge stream, the improvement which comprises sweeping oxygen generated by the decomposition with at least part of said vapor stream.

2. The process of claim 1 wherein a solid catalyst is used for decomposing peroxidic materials.

3. The process of claim 1 wherein a homogeneous catalyst is used for decomposing peroxidic materials.

4. The process of claim 1 wherein iron (III) acetylacetonate is used for decomposing peroxidic materials.

* * * * *